(12) United States Patent
Hanson et al.

(10) Patent No.: US 11,931,060 B2
(45) Date of Patent: Mar. 19, 2024

(54) ASPIRATION MEDICAL DEVICE

(71) Applicant: BOSTON SCIENTIFIC SCIMED, INC., Maple Grove, MN (US)

(72) Inventors: Cass Alexander Hanson, St. Paul, MN (US); Benjamin Michael Wilke, Circle Pines, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 102 days.

(21) Appl. No.: 16/245,130

(22) Filed: Jan. 10, 2019

(65) Prior Publication Data

US 2019/0209745 A1 Jul. 11, 2019

Related U.S. Application Data

(60) Provisional application No. 62/615,766, filed on Jan. 10, 2018.

(51) Int. Cl.
| | | |
|---|---|---|
| *A61B 17/3203* | (2006.01) | |
| *A61B 17/22* | (2006.01) | |
| *A61M 1/00* | (2006.01) | |
| *A61M 3/02* | (2006.01) | |
| *A61M 25/00* | (2006.01) | |

(52) U.S. Cl.
CPC .... *A61B 17/32037* (2013.01); *A61B 17/3203* (2013.01); *A61M 1/77* (2021.05); *A61M 3/0279* (2013.01); *A61B 2017/22079* (2013.01); *A61B 2017/22084* (2013.01);
(Continued)

(58) Field of Classification Search
CPC ........ A61B 17/32037; A61B 2217/007; A61B 2017/22068; A61B 2017/22079; A61B 2217/005; A61M 25/0026; A61M 25/007; A61M 25/0068; A61M 2025/0073; A61M 2025/0004; A61M 25/10
See application file for complete search history.

(56) References Cited

U.S. PATENT DOCUMENTS 2,568,566 A * 9/1951 Sokolik .................. A61M 1/77
604/35
5,312,356 A 5/1994 Engelson et al.
(Continued)

FOREIGN PATENT DOCUMENTS

| EP | 0788774 A1 | 8/1997 |
|---|---|---|
| EP | 1092396 A2 | 4/2001 |

(Continued)

OTHER PUBLICATIONS

Invitation to Pay Additional Fees dated Apr. 21, 2017 for International Application No. PCT/US2017/020717.
(Continued)

*Primary Examiner* — Lauren P Farrar
(74) *Attorney, Agent, or Firm* — Seager, Tufte & Wickhem, LLP

(57) ABSTRACT

Aspiration medical device as well as methods for making and using aspiration medical devices are disclosed. An example aspiration medical device may include a tubular member having a distal end region and defining an inflow orifice adjacent to the distal end region. An aspiration member may be disposed within the tubular member. The aspiration member may have a plurality of axially-spaced fluid jets formed therein.

20 Claims, 11 Drawing Sheets

(52) U.S. Cl.
CPC ... *A61B 2217/005* (2013.01); *A61B 2217/007* (2013.01); *A61M 25/007* (2013.01)

(56) References Cited

U.S. PATENT DOCUMENTS

| | | | |
|---|---|---|---|
| 5,425,723 A * | 6/1995 | Wang | A61M 25/007 |
| | | | 604/523 |
| 5,976,103 A * | 11/1999 | Martin | A61M 25/0026 |
| | | | 604/284 |
| 5,989,271 A * | 11/1999 | Bonnette | A61B 17/32037 |
| | | | 604/22 |
| 7,226,433 B2 | 6/2007 | Bonnette et al. | |
| 8,998,843 B2 | 4/2015 | Bonnette et al. | |
| 9,078,691 B2 | 7/2015 | Morris et al. | |
| 2004/0073141 A1 | 4/2004 | Hartley et al. | |
| 2006/0129091 A1 * | 6/2006 | Bonnette | A61B 17/22 |
| | | | 604/93.01 |
| 2006/0135870 A1 | 6/2006 | Webler | |
| 2008/0188831 A1 | 8/2008 | Bonnette et al. | |
| 2008/0275383 A1 * | 11/2008 | Weisel | A61B 17/32037 |
| | | | 604/35 |
| 2011/0015564 A1 * | 1/2011 | Bonnette | A61M 25/0068 |
| | | | 606/159 |
| 2013/0267891 A1 * | 10/2013 | Malhi | A61B 17/32037 |
| | | | 604/30 |
| 2014/0155830 A1 | 6/2014 | Bonnette et al. | |
| 2014/0228869 A1 | 8/2014 | Bonnette et al. | |
| 2014/0277006 A1 * | 9/2014 | Bonnette | A61B 17/32037 |
| | | | 606/159 |
| 2014/0343457 A1 | 11/2014 | Shekalim et al. | |
| 2017/0252057 A1 | 9/2017 | Bonnette et al. | |
| 2018/0235648 A1 | 8/2018 | Wilke et al. | |

FOREIGN PATENT DOCUMENTS

| | | | | |
|---|---|---|---|---|
| EP | 2712559 A2 | 4/2014 | | |
| WO | 9613295 A1 | 5/1996 | | |
| WO | WO-0151116 A2 * | 7/2001 | | A61M 25/007 |
| WO | 2008097993 A2 | 8/2008 | | |
| WO | 2017152086 A1 | 9/2017 | | |

OTHER PUBLICATIONS

International Search Report and Written Opinion for Application No. PCT/US2018/018762, 14 pages, dated Apr. 20, 2018.
International Search Report and Written Opinion for Application No. PCT/US2019/013108, 12 pages, dated Apr. 18, 2019.

* cited by examiner

ASPIRATION MEDICAL DEVICE

CROSS-REFERENCE TO RELATED APPLICATIONS

This application claims the benefit of priority under 35 U.S.C. § 119 of U.S. Provisional Application No. 62/615,766, filed Jan. 10, 2018, the entire disclosure of which is hereby incorporated by reference.

TECHNICAL FIELD

The present disclosure pertains to medical devices, and methods for manufacturing medical devices. More particularly, the present disclosure pertains to aspiration medical devices.

BACKGROUND

A wide variety of medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An aspiration medical device is disclosed. The aspiration medical device comprises: a tubular member having a distal end region and defining an inflow orifice adjacent to the distal end region; and an aspiration member disposed within the tubular member, the aspiration member having a plurality of axially-spaced fluid jets formed therein.

Alternatively or additionally to any of the embodiments above, the tubular member has an outflow orifice disposed proximally of the inflow orifice.

Alternatively or additionally to any of the embodiments above, the aspiration member has a closed distal end.

Alternatively or additionally to any of the embodiments above, the plurality of axially-spaced fluid jets are designed to infuse fluid within the tubular member in a proximal direction.

Alternatively or additionally to any of the embodiments above, the plurality of axially-spaced fluid jets are designed to infuse fluid within the tubular member in a direction that is offset from a longitudinal axis of the aspiration member at an angle.

Alternatively or additionally to any of the embodiments above, the angle is greater than zero degrees and less than ninety degrees.

Alternatively or additionally to any of the embodiments above, the plurality of axially-spaced fluid jets are axially aligned along the aspiration member.

Alternatively or additionally to any of the embodiments above, at least some of the plurality of axially-spaced fluid jets are circumferentially offset from one another along the aspiration member.

Alternatively or additionally to any of the embodiments above, further comprising an outer sleeve disposed along the tubular member.

Alternatively or additionally to any of the embodiments above, a fluid infusion lumen is defined between the outer sleeve and the tubular member.

Alternatively or additionally to any of the embodiments above, the distal end region of the tubular member includes an open distal end.

Alternatively or additionally to any of the embodiments above, the distal end region of the tubular member includes an angled distal end.

Alternatively or additionally to any of the embodiments above, the distal end region of the tubular member includes a flared distal end.

An aspiration catheter is disclosed. The aspiration catheter comprises: a catheter shaft defining a lumen; and an aspiration member disposed within the lumen, the aspiration member including a shaft and a plurality of fluid jet orifices disposed along the shaft.

Alternatively or additionally to any of the embodiments above, the catheter shaft has a distal end and an inflow orifice disposed proximally of the distal end.

Alternatively or additionally to any of the embodiments above, the plurality of fluid jet orifices are designed to infuse fluid within the lumen in a proximal direction.

Alternatively or additionally to any of the embodiments above, the plurality of fluid jet orifices are designed to proximally infuse fluid within the lumen in a direction that is offset from a longitudinal axis of the shaft at an acute angle.

Alternatively or additionally to any of the embodiments above, further comprising an outer sleeve disposed along the catheter shaft, wherein a fluid infusion lumen is defined between the outer sleeve and the catheter shaft.

A method for aspirating material from a blood vessel is disclosed. The method comprises: disposing an aspiration catheter adjacent to a stenosis, the aspiration catheter comprising: a catheter shaft defining a lumen, and an aspiration member disposed within the lumen, the aspiration member including a shaft and a plurality of fluid jet orifices disposed along the shaft; and infusing fluid through the plurality of fluid jet orifices to aspirate the stenotic material.

Alternatively or additionally to any of the embodiments above, infusing fluid through the plurality of fluid jet orifices to aspirate the stenotic material includes infusing fluid within the lumen in a proximal direction.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
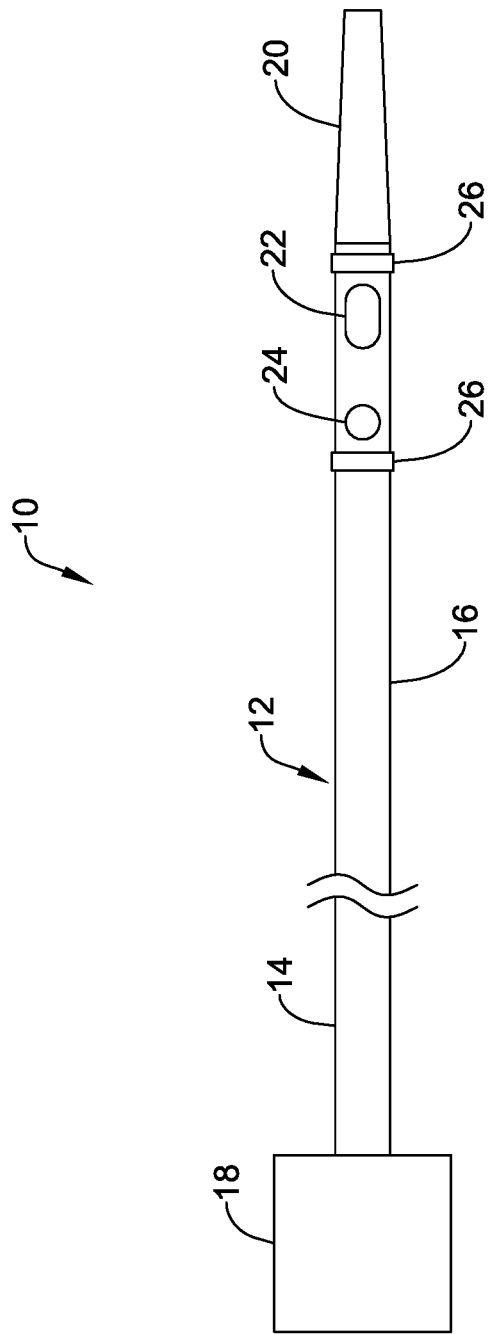
FIG. 1 is a side view of an example aspiration medical device.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

FIG. 1 is a side view of an example aspiration medical device 10. The aspiration medical device 10 may include a tubular member or catheter shaft 12 having a proximal end region 14 and a distal end region 16. A hub or manifold 18 (depicted schematically) may be coupled to the proximal end region 14. A tip member 20 may be coupled to the distal end region 16. The catheter shaft 12 may include a number of additional features. For example, one or more markers 26 (e.g., radiopaque marker bands) may be disposed along the catheter shaft 12.

The catheter shaft 12 may have a plurality of openings or orifices. For example, the catheter shaft 12 may have a first or inflow orifice 22. The inflow orifice 22 may be disposed proximally of the distal end of the catheter shaft. The catheter shaft 12 may also include a second or outflow orifice 24. The outflow orifice 24 may be disposed proximally of the inflow orifice 22. In some instances, the inflow orifice 22 and the outflow orifice 24 may be axially aligned along the catheter shaft 12. In other instances, the inflow orifice 22 and the outflow orifice 24 may be circumferentially offset from one another about the catheter shaft 12. In some instances, the inflow orifice 22 and the outflow orifice 24 may have the same size, shape, or both. In other instances, the inflow orifice 22 and the outflow orifice 24 may differ in size, shape, or both.

Figure 2:
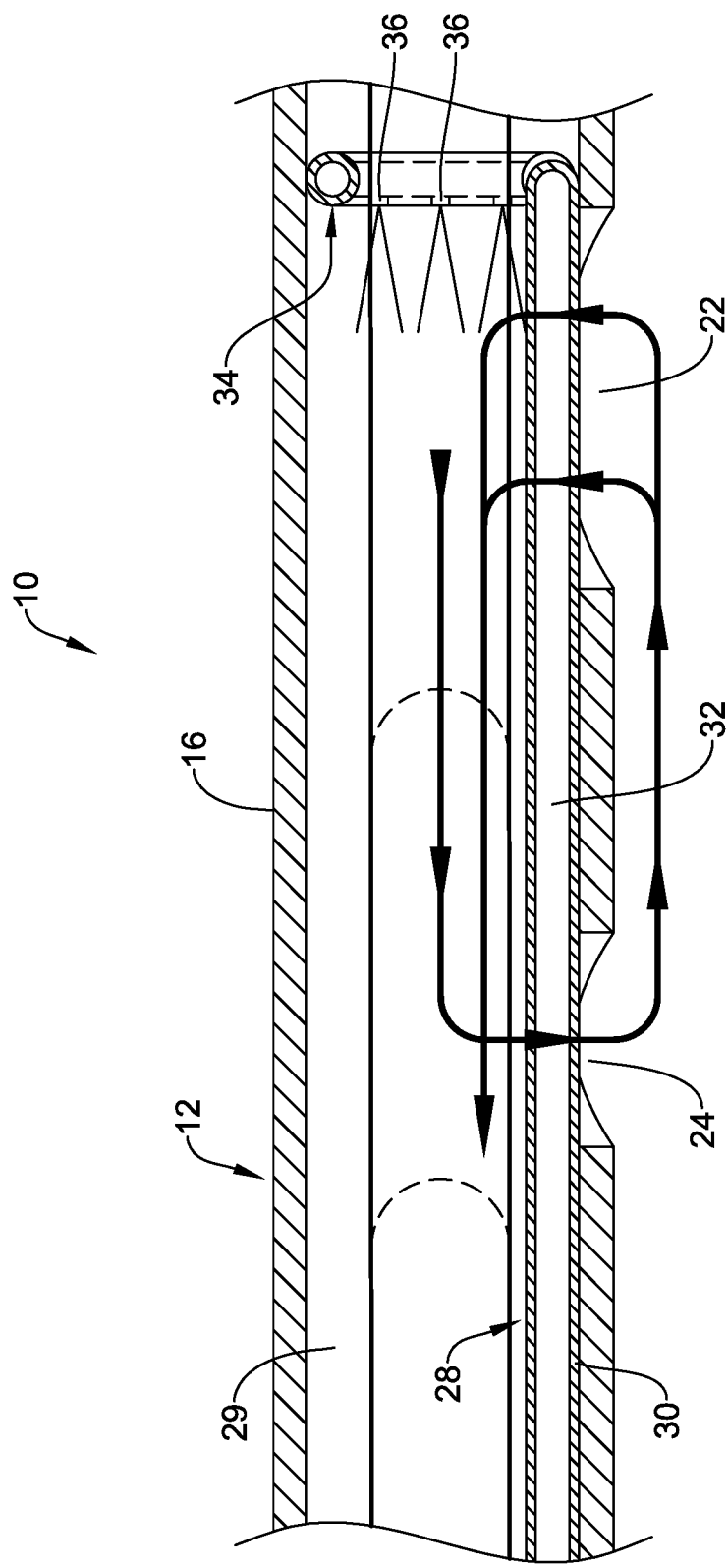
FIG. 2 is a cross-sectional side view of a portion of an example aspiration medical device.

FIG. 2 is a cross-sectional view of a portion of the aspiration medical device 10 that schematically depicts how the aspiration medical device 10 may be used to aspirate material (e.g., embolic material, thrombus/thrombogenic material, stenotic material, etc.) from a patient. Here it can be seen that an aspiration assembly 28 may be disposed within a lumen 29 of the catheter shaft 12. The aspiration assembly 28 may include a tubular member or inner tube 30 defining a lumen 32. A fluid jet 34 may be coupled to the inner tube 30. The fluid jet 34 may be in fluid communication with the lumen 32. In some instances, the fluid jet 34 may be oriented at an angle relative to the inner tube 30. For example, the fluid jet 34 may be disposed at an angle that is normal to the inner tube 30. In at least some instances, the fluid jet 34 may have an annular arrangement. However, other arrangements and/or configurations are contemplated.

The fluid jet 34 may have one or more jet orifices 36 define therein. In some instances, the fluid jet 34 includes one jet orifice 36. In other instances, the fluid jet 34 may include two, three, four, five, six, seven, eight, or more jet orifices 36. The jet orifices 36 may take the form of openings in the fluid jet 34 that allow fluid infused through the lumen 32 to be jetted in a generally proximal direction within the lumen 29 of the catheter shaft 12 as depicted by lines in FIG. 2 projecting proximally from the jet orifices 36. The jet orifices 36 may be spaced evenly along the fluid jet 34. Alternatively, the jet orifices may be arranged in an uneven manner or distributed along only a portion of the fluid jet 34.

Infusion of a fluid (e.g., a motive fluid, a liquid, a gas or air, steam, a fluid with particles disposed therein, or the like) though the lumen 32 of the inner tube 30 may cause the fluid to be jetted or otherwise exit the jet orifices 36. As the fluid moves proximally through the lumen 29, the fluid may generate an aspiration force that can draw entrainment material into the lumen 29 through the inflow orifice 22. The material drawn into the lumen 29 may be aspirated through the lumen 29 and out from a patient. In addition or in the alternative, some or all of the thrombogenic material drawn into the lumen 29 may exit that catheter shaft 12 through the outflow orifice 24. The material may recirculate and the action of recirculation may help to break up the thrombogenic material in order to ease removal. For example, the material may enter the inflow orifice 22 where it can be aspirated from the patient and/or further recirculated.

In some instances, it may be desirable to enhance the aspiration force generated within the catheter shaft 12. Disclosed herein are aspiration medical devices that may generate desirable aspiration forces, which may enhance aspiration.

Figure 3:
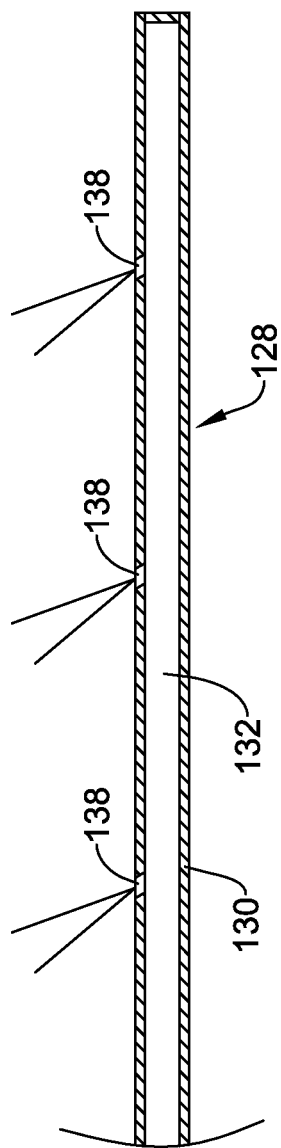
FIG. 3 is a cross-sectional side view of a portion of an example aspiration member.
Figure 4:
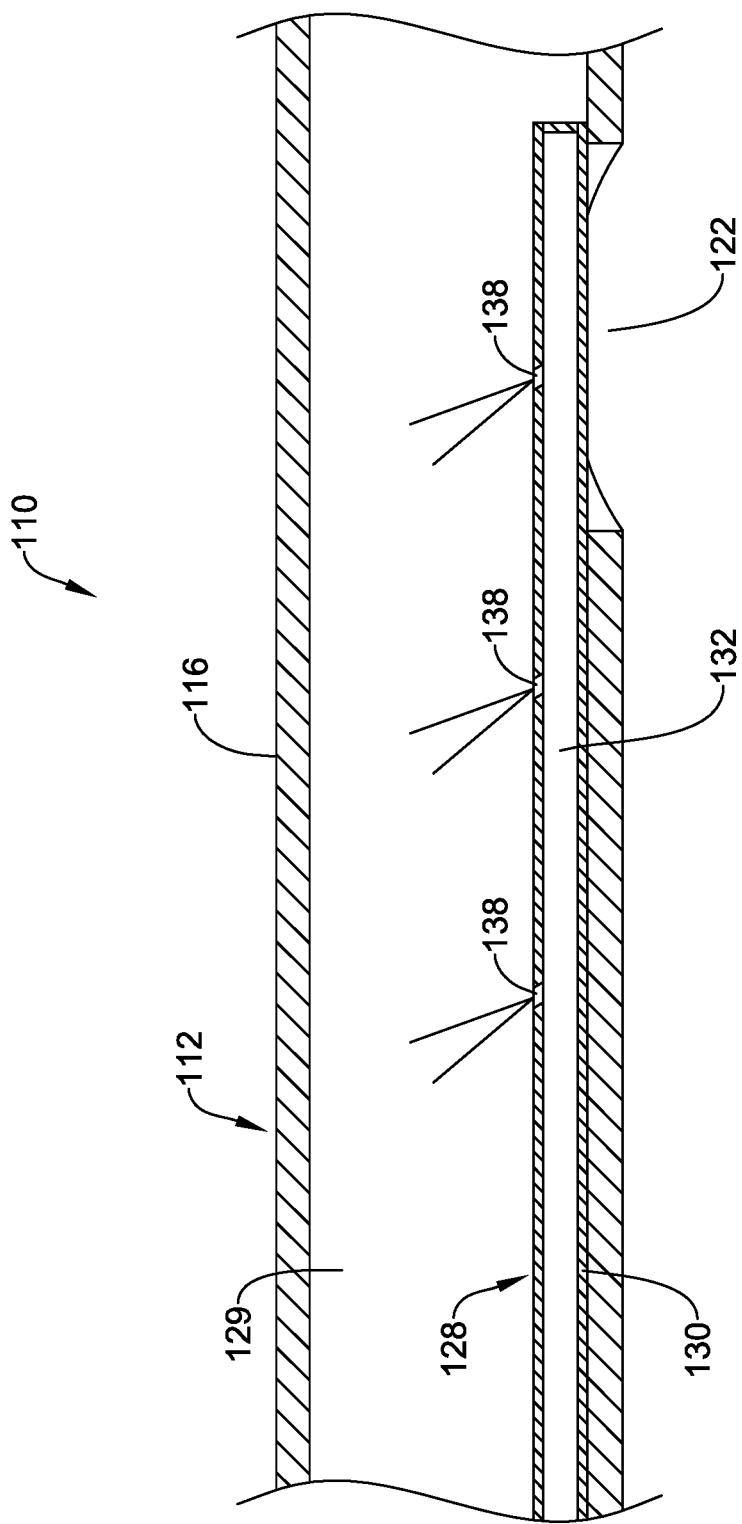
FIG. 4 is a cross-sectional side view of a portion of an example aspiration medical device.

FIGS. 3-4 illustrates an example aspiration member 128 (e.g., that may be similar in form and function to other aspiration members/assemblies disclosed herein) that may be used in an aspiration medical device 110. The aspiration medical device 110 (e.g., a portion of which is depicted in FIG. 4) may be similar in form and function to other aspiration medical devices disclosed herein. For example, the aspiration medical device 110 may include a catheter shaft 112 having a distal end region 116 and defining a lumen 129. A first or inflow orifice 122 may be defined in the catheter shaft 112.

An aspiration member 128 may be disposed in the lumen 129 of the catheter shaft 112. The aspiration member 128 may include a shaft 130 defining a lumen or fluid pathway 132. In at least some instances, the aspiration member 128 has a closed distal end. Because of this, fluid may be able to pass through the fluid pathway 132 but not exit the distal end the same way fluid may pass through the distal opening of a tube. Furthermore, the aspiration member 128 may differ from the aspiration assembly 28 (e.g., as shown in FIG. 2) in that the aspiration member 128 may lack a fluid jet 34.

A plurality of jet orifices 138 may be defined along the shaft 130. For example, the shaft 130 may include two, three, four, five, six, or more jet orifices 138. In some instances, some or all of the jet orifices 138 may be axially aligned along the shaft 130. In other instances, one or more of the jet orifices 138 may be circumferentially offset from one another about the shaft 130. A number of patterns are contemplated including a helical pattern, a regular pattern where no two jet orifices 138 are disposed at the same axial location, a regular pattern including two or more jet orifices 138 disposed at the same axial location, an irregular pattern (where some of the jet orifices 138 may or may not be disposed at the same axial location), etc. The jet orifices 138 may be formed using a suitable method such as electron discharge machining, etching, cutting (e.g., including laser cutting), or the like. In some instances, one or more of the jet orifices 138 have a substantially round shape. In other instances, one or more of the jet orifices 138 have a substantially non-round shape (e.g., oval, polygonal, irregular, etc.). In some instances, the jet orifices 138 may be beveled or otherwise include a beveled surface.

The jet orifices 138 may be designed to infuse fluid (e.g., a motive fluid, a liquid, a gas or air, steam, a fluid with particles disposed therein, or the like) through the jet orifices 138 and into the lumen 129 of the catheter shaft 112 in a generally proximal direction as depicted by lines projecting generally proximally from the jet orifices 138 in FIGS. 3-4. In some instances, the jet orifices 138 may be oriented at an angle relative to the longitudinal axis of the shaft 130. For example, the jet orifices 138 may be oriented at an acute angle relative to the longitudinal axis of the shaft 130 and/or oriented at an angle greater than zero degrees and less than ninety degrees relative to the longitudinal axis of the shaft 130. In other instances, the jet orifices 138 may be oriented at ninety degrees relative to the longitudinal axis of the shaft 130. The angle may or may not be the same for all the jet orifice 138. Infusion of motive fluid through the lumen 132 of the shaft 130 may result in fluid being jetted through the jet orifices 138 (e.g., generally in the proximal direction) and the generation of an aspiration force.

In at least some instances, the jet orifices 138 may be understood as being arranged in series. In other words, the jet orifices 138 may be arranged at various locations along the longitudinal axis of the shaft 130. This may position the jet orifices 138 at spaced apart axially locations within the catheter shaft 112. Accordingly, motive fluid leaves via the jet orifices forming a jetted motive fluid. This Jetted motive fluid enters an entrainment material where the shear layer between the two causes turbulence, mixing, and transfer of momentum. Entrainment material may enter the inflow orifice 122 and then may be urged proximally by momentum transfer. As the mixture of jetted motive fluid and entrainment material migrates proximally, the material may sequentially approach a number of jet orifices 138. Upon interaction with the jetted motive fluid from each individual jet orifice 138, the momentum in the entrainment material mixture may increase, and the thrombogenic material may more readily flow through the catheter shaft 112 for removal. The increase in momentum may allow for the catheter shaft 112 to be used without a second or outflow orifice (e.g., positioned proximally of the inflow orifice 122 and that may be similar to the outflow orifice 24 as depicted in FIG. 2). Alternatively, some of the entrapped thrombogenic material may exit the catheter shaft 112 through a second orifice (not shown) positioned proximally of the inflow orifice 122, recirculate to the inflow orifice 122 (e.g., one or more times), and then move through the lumen 129.

Figure 5:
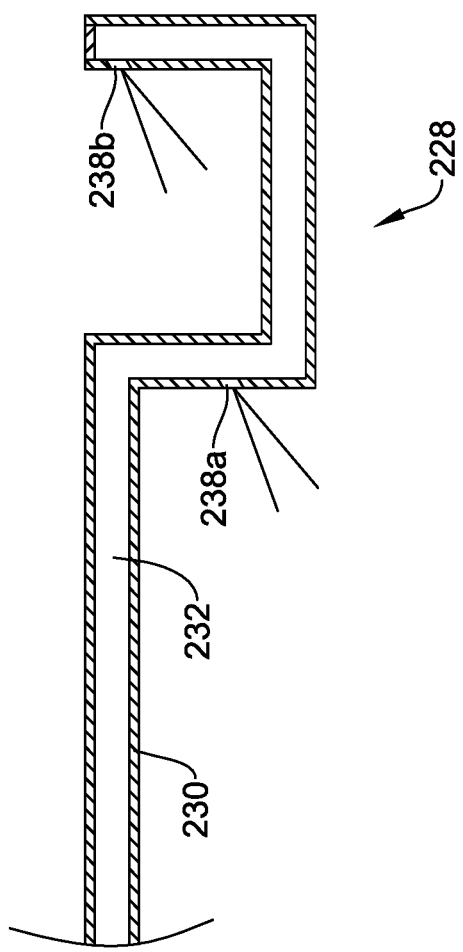
FIG. 5 is a cross-sectional side view of a portion of an example aspiration member.

While a plurality of jet orifices 138 arranged in series may be desirable, a number of additional arrangements are contemplated. For example, FIG. 5 illustrates another example aspiration member 228 that may be similar in form and function to other aspiration members disclosed herein. The aspiration member 228 may include a shaft 230 having a lumen or fluid pathway 232 formed therein. In this example, the aspiration member includes a plurality of jet orifices 238a, 238b that may be described as being arranged in series. For example, the jet orifices 238a, 238b may be formed on opposite sides of the shaft 230. In such instances, the shaft 230 may include one or more bends or curves so that the jet orifices 238a, 238b may generally be oriented in a proximal direction.

Figure 6:
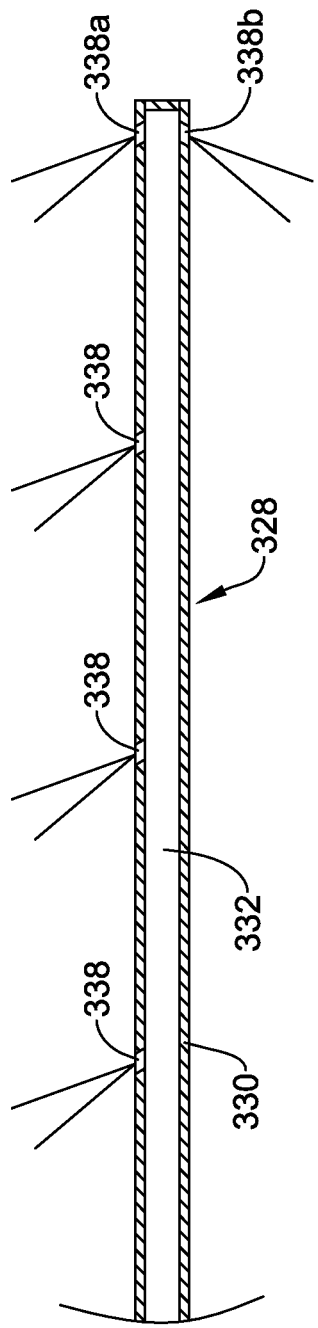
FIG. 6 is a cross-sectional side view of a portion of an example aspiration member.

FIG. 6 illustrates another example aspiration member 328 that may be similar in form and function to other aspiration members disclosed herein. The aspiration member 328 may include a shaft 330 having a lumen or fluid pathway 332 formed therein. In this example, the aspiration member includes a plurality of jet orifices 338 including a first jet orifice 338a on a first side of the shaft 330 and a second jet orifice 338b on a second side of the shaft 330. The first jet orifice 338a and the second jet orifice 338b may be described as having a parallel arrangement with each other while together they are in series arrangement with the remaining jet orifices 338. Thus, this aspiration member 328 depicts a jet orifice arrangement containing in series and parallel arrays. Other aspiration members are contemplated that are capable of infusing fluid in multiple directions.

Figure 7:
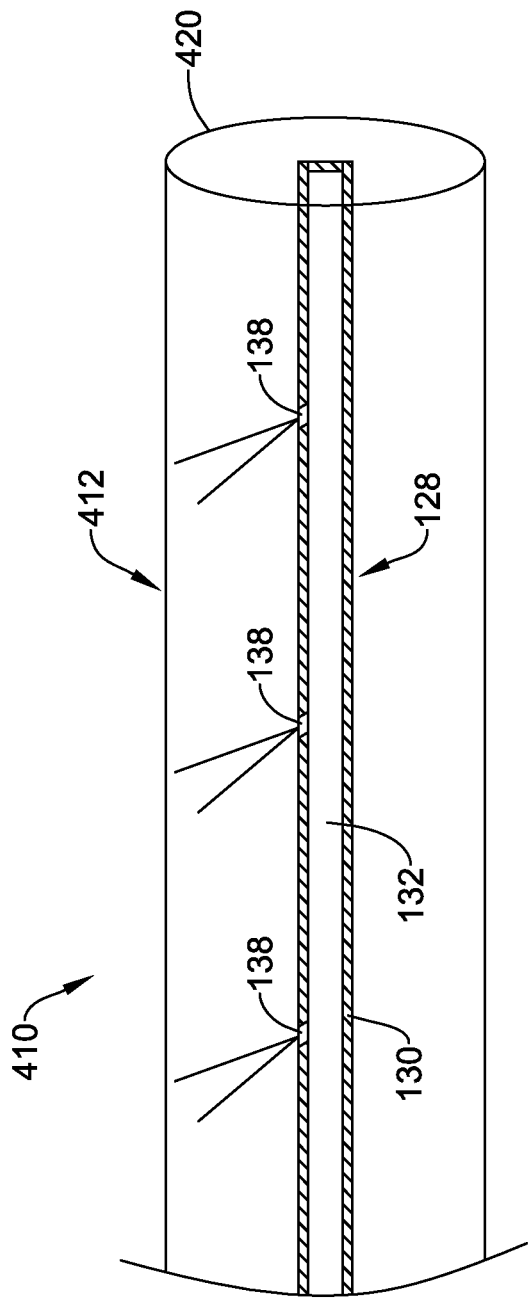
FIG. 7 is a cross-sectional side view of a portion of an example aspiration medical device.
Figure 8:
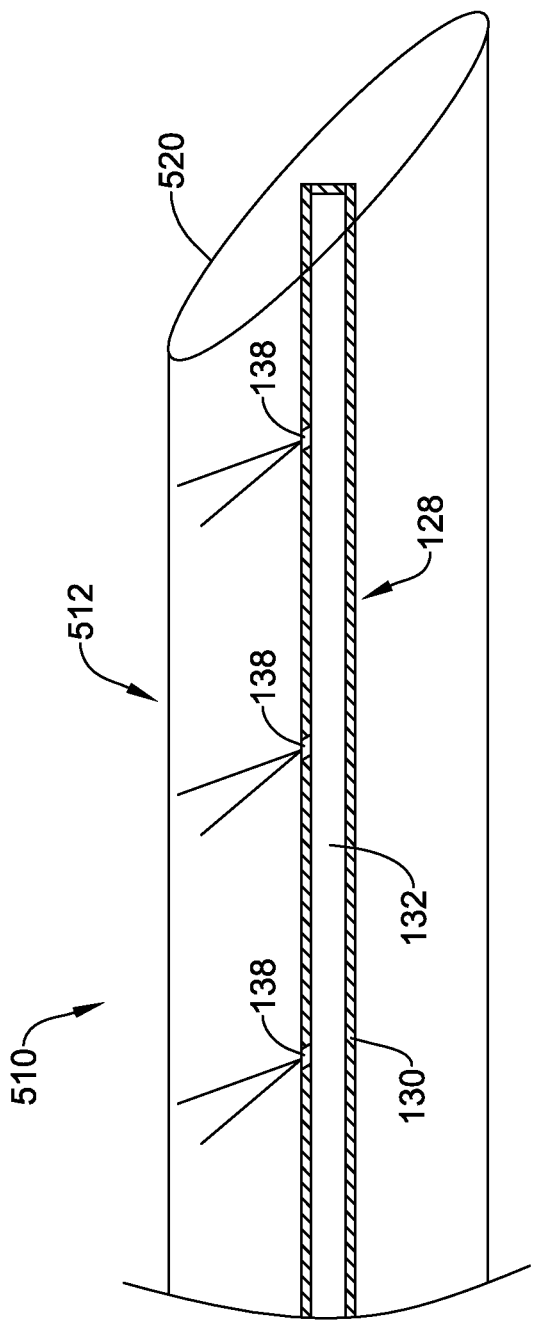
FIG. 8 is a cross-sectional side view of a portion of an example aspiration medical device.
Figure 9:
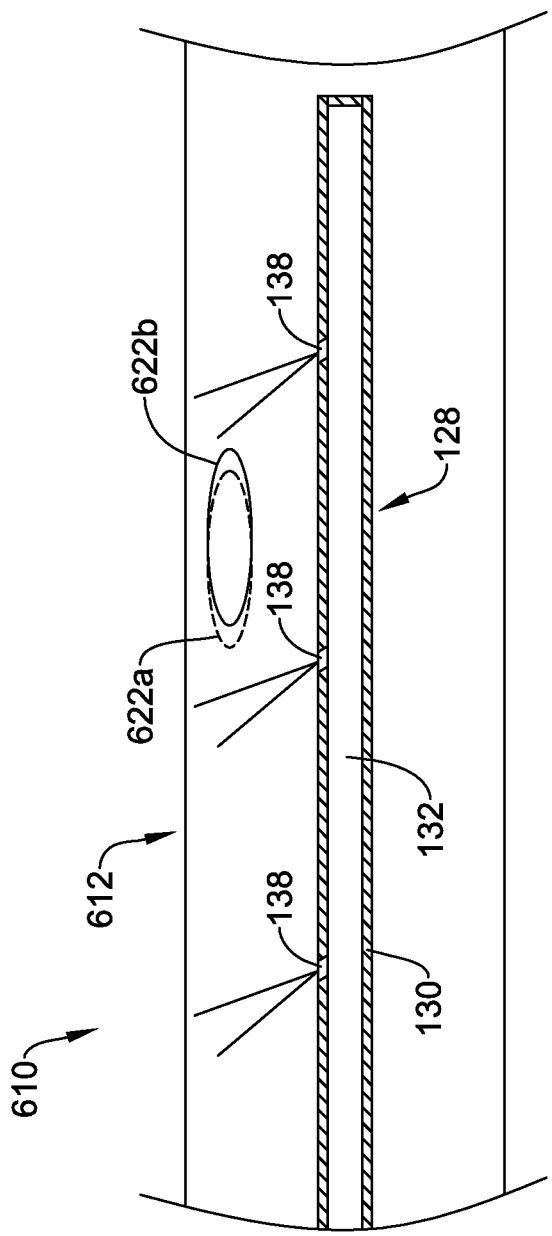
FIG. 9 is a cross-sectional side view of a portion of an example aspiration medical device.
Figure 10:
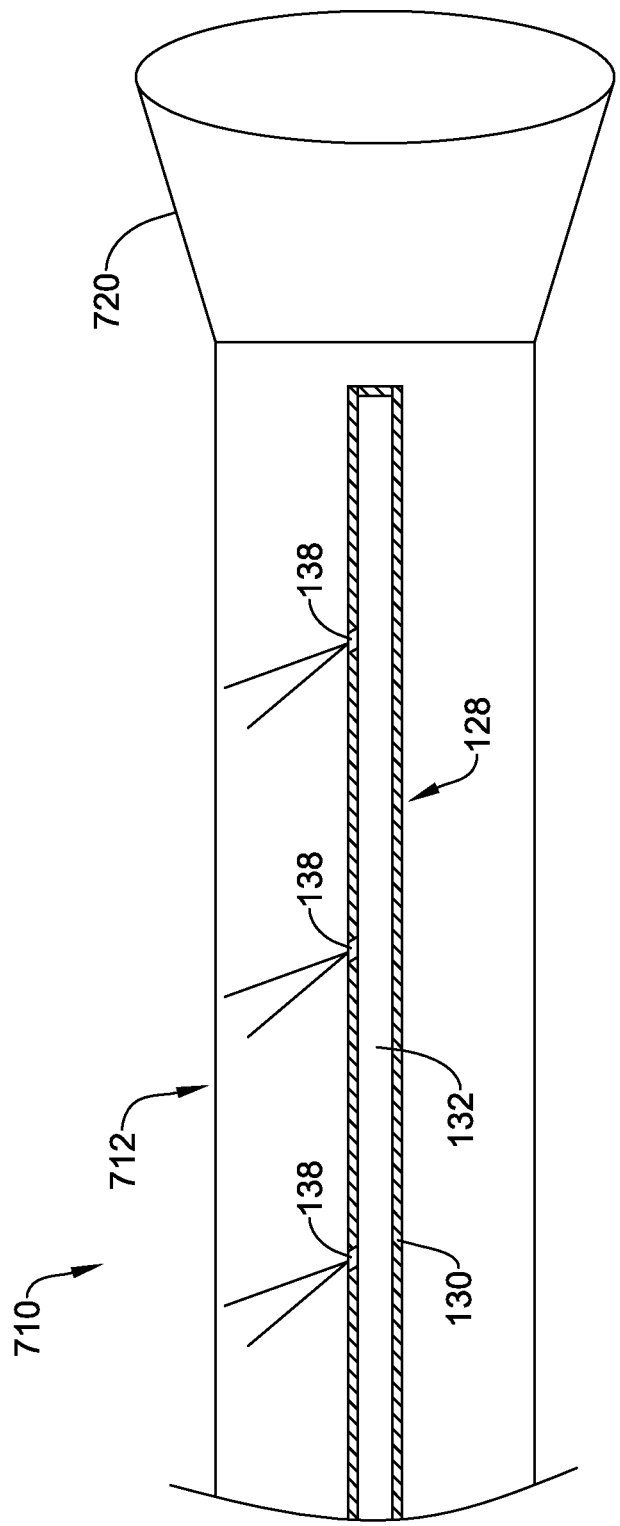
FIG. 10 is a cross-sectional side view of a portion of an example aspiration medical device.

In FIG. 4, the catheter shaft 112 (e.g., similar to the catheter shaft 12) is shown with the inflow orifice 122. Other catheter shafts are contemplated, for example, such as those shown in FIGS. 7-10 with differing arrangements. For example, FIG. 7 illustrates an example medical device 410 that includes a catheter shaft 412 with an open distal end 420. FIG. 8 illustrates an example medical device 510 that includes a catheter shaft 512 with an angled distal end 520. FIG. 9 illustrates an example medical device 610 that includes a catheter shaft 612 with a plurality of inflow orifices 622a, 622b. FIG. 10 illustrates an example medical device 710 that includes a catheter shaft 712 with flared distal end 720. These are just some of the catheter shafts contemplated. As appropriate, these example catheter shafts can be used with any of the aspiration members disclosed herein.

Figure 11:
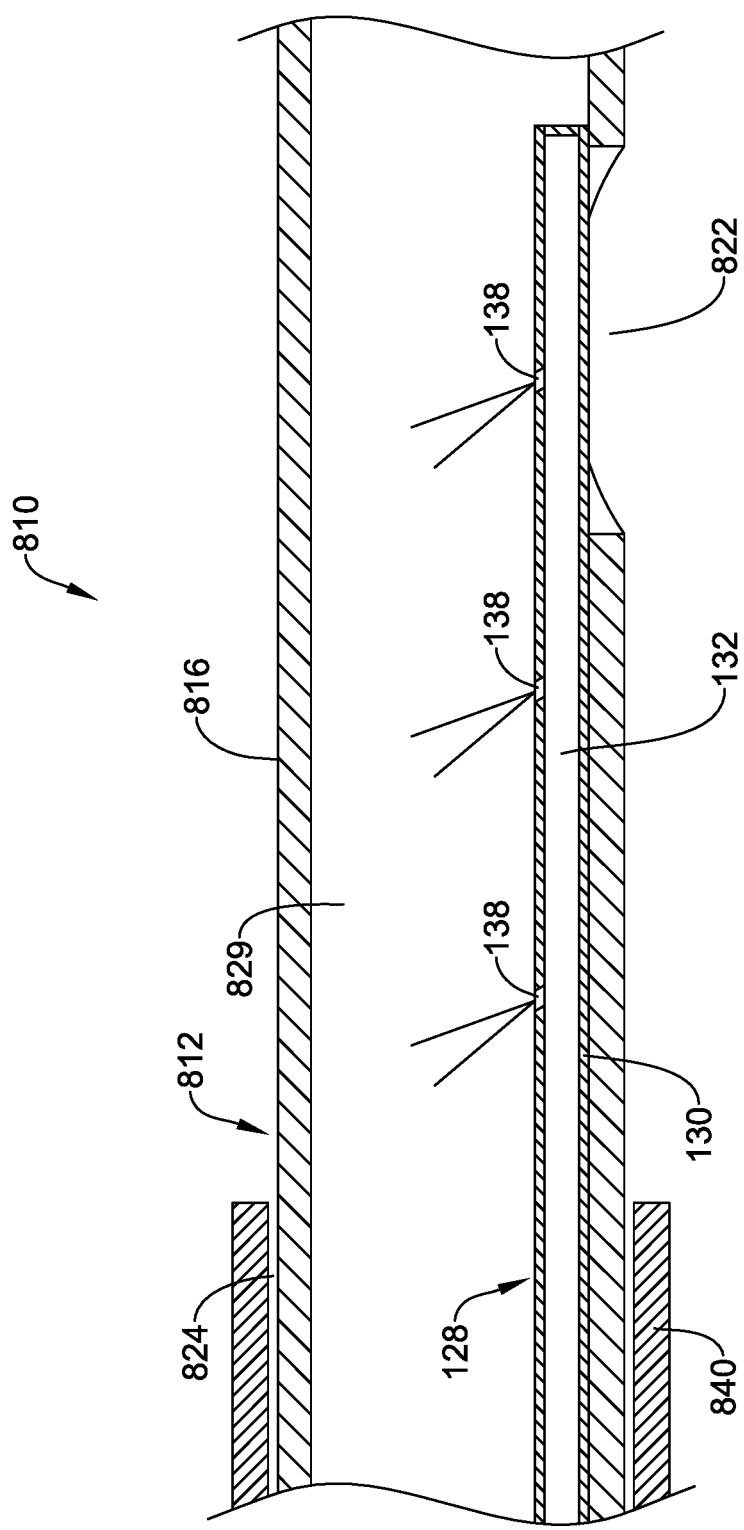
FIG. 11 is a cross-sectional side view of a portion of an example aspiration medical device.

FIG. 11 illustrates an aspiration medical device 810 that may be similar in form and function to other aspiration medical devices disclosed herein. The aspiration medical device 810 may including a catheter shaft 812 having a distal end region 816 and defining a lumen 829. A first or inflow orifice 822 may be defined in the catheter shaft 812. An aspiration member (in this example, the aspiration member 128 is shown) 228 may be disposed in the lumen 829 of the catheter shaft 812.

In some instances, it may be desirable to replenish or otherwise balance the amount of material, fluid, and/or blood that may be removed during an aspiration procedure. In order to provide a mechanism to infuse fluid (e.g., to balance the fluid/material removed), an outer sleeve 840 may be disposed along the catheter shaft 812. A fluid infusion lumen 824 may be defined between the inner surface of the outer sleeve 840 and the outer surface of the catheter shaft 812. During an aspiration procedure, fluid may be infused through the fluid infusion lumen 842. This may help to balance the fluid/material removed. In some of these and in other instances, the fluid infusion lumen 842 may also be used to infuse a therapeutic agent (e.g., such as a drug, lytic, or the like).

The materials that can be used for the various components of the aspiration medical device 10 (and/or other aspiration medical devices disclosed herein) and the various components thereof may include those commonly associated with medical devices. For simplicity purposes, the following discussion makes reference to the catheter shaft 12 of the aspiration medical device 10. However, this is not intended to limit the devices and methods described herein, as the discussion may be applied to other catheter shaft and/or components of any of the aspiration medical devices disclosed herein.

The catheter shaft 12 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the catheter shaft 12 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the catheter shaft 12 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the catheter shaft 12 to achieve the same result.

In some embodiments, a degree of Magnetic Resonance Imaging (MRI) compatibility is imparted into the catheter shaft 12. For example, the catheter shaft 12, or portions thereof, may be made of a material that does not substantially distort the image and create substantial artifacts (e.g., gaps in the image). Certain ferromagnetic materials, for example, may not be suitable because they may create artifacts in an MRI image. The catheter shaft 12, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

U.S. Patent Application Pub. No. US 2017/0252057 is incorporated herein by reference.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. An aspiration medical device, comprising:
a tubular member having a distal end region and defining an inflow orifice adjacent to the distal end region;
an aspiration member disposed within the tubular member, the aspiration member having a plurality of fluid jets formed therein;
wherein the aspiration medical device has a longitudinal axis and wherein the plurality of fluid jets and spaced apart along the longitudinal axis;
wherein the plurality of fluid jets are defined by openings formed in a wall of the aspiration member, the openings being oriented at an acute angle relative to a longitudinal axis of the aspiration member so as to infuse fluid within the tubular member in a proximal direction that is offset from the longitudinal axis of the aspiration member at an angle;
wherein the angle is greater than zero degrees and less than ninety degrees; and
wherein the plurality of fluid jets are configured as high-pressure fluid jets that infuse a high-pressure fluid within the tubular member and wherein the tubular member substantially prevents the high-pressure fluid from damaging tissue.

2. The aspiration medical device of claim 1, wherein the tubular member has an outflow orifice disposed proximally of the inflow orifice.

3. The aspiration medical device of claim 1, wherein the aspiration member has a closed distal end.

4. The aspiration medical device of claim 1, wherein the plurality of fluid jets are axially aligned along the aspiration member.

5. The aspiration medical device of claim 1, wherein at least some of the plurality of fluid jets are circumferentially offset from one another along the aspiration member.

6. The aspiration medical device of claim 1, further comprising an outer sleeve disposed along the tubular member.

7. The aspiration medical device of claim 6, wherein a fluid infusion lumen is defined between the outer sleeve and the tubular member.

8. The aspiration medical device of claim 1, wherein the distal end region of the tubular member includes an open distal end.

9. The aspiration medical device of claim 1, wherein the distal end region of the tubular member includes an angled distal end.

10. The aspiration medical device of claim 1, wherein the distal end region of the tubular member includes a flared distal end.

11. The aspiration medical device of claim 1, wherein the aspiration member has a width and a length greater than the width.

12. The aspiration medical device of claim 1, wherein the aspiration member comprises an elongate tube offset from a central axis of the tubular member and positioned adjacent to a wall surface of the tubular member.

13. The aspiration medical device of claim 1, wherein the aspiration member including a longitudinally-extending shaft portion and wherein the plurality of fluid jets are disposed along the longitudinally-extending shaft portion.

14. An aspiration catheter, comprising:
a catheter shaft defining a lumen;
an aspiration member disposed within the lumen, the aspiration member including a longitudinally-extending shaft portion and a plurality of fluid jet orifices disposed along the longitudinally-extending shaft portion;
wherein the plurality of fluid jet orifices includes a first fluid jet orifice and a second fluid jet orifice disposed distally of the first fluid jet orifice;
wherein the first fluid jet orifice is defined by an opening formed in a wall of the aspiration member, the opening being oriented proximally and at an acute angle relative to a longitudinal axis of the aspiration member; and
wherein the first fluid jet orifice and the second fluid jet orifice are configured as high-pressure fluid jet orifices that infuse a high-pressure fluid within the catheter shaft.

15. The aspiration catheter of claim 14, wherein the catheter shaft has a distal end and an inflow orifice disposed proximally of the distal end.

16. The aspiration catheter of claim 14, wherein the plurality of fluid jet orifices are designed to infuse fluid within the lumen in a proximal direction.

17. The aspiration catheter of claim 14, wherein the plurality of fluid jet orifices are designed to proximally infuse fluid within the lumen in a direction that is offset from a longitudinal axis of the shaft at an acute angle.

18. The aspiration catheter of claim 14, further comprising an outer sleeve disposed along the catheter shaft, wherein a fluid infusion lumen is defined between the outer sleeve and the catheter shaft.

19. A method for aspirating material from a blood vessel, the method comprising:
disposing an aspiration catheter adjacent to a stenosis, the aspiration catheter comprising:
a catheter shaft defining a lumen, and
an aspiration member disposed within the lumen, the aspiration member including a longitudinally-extending shaft portion and a plurality of fluid jet orifices disposed along the longitudinally-extending shaft portion;
wherein the plurality of fluid jet orifices includes a first fluid jet orifice and a second fluid jet orifice disposed distally of the first fluid jet orifice,
wherein the first fluid jet orifice and the second fluid jet orifice are configured as high-pressure fluid jet orifices that infuse a high-pressure fluid within the catheter shaft,
wherein the first fluid jet orifice is defined by an opening formed in a wall of the aspiration member, the opening being oriented proximally and at an acute angle relative to a longitudinal axis of the aspiration member; and
infusing fluid through the plurality of fluid jet orifices to aspirate the stenosis.

20. The method of claim 19, wherein infusing fluid through the plurality of fluid jet orifices to aspirate the stenosis includes infusing fluid within the lumen in a proximal direction.

* * * * *